(12) United States Patent
Richmond et al.

(10) Patent No.: US 6,937,904 B2
(45) Date of Patent: Aug. 30, 2005

(54) SYSTEM AND METHOD FOR PROVIDING RECOVERY FROM MUSCLE DENERVATION

(75) Inventors: Frances J. R. Richmond, South Pasadena, CA (US); Gerald E. Loeb, South Pasadena, CA (US); Tessa Gordon, Edmonton (CA)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 405 days.

(21) Appl. No.: 10/022,562

(22) Filed: Dec. 12, 2001

(65) Prior Publication Data

US 2002/0120309 A1 Aug. 29, 2002

Related U.S. Application Data

(60) Provisional application No. 60/255,284, filed on Dec. 13, 2000.

(51) Int. Cl.[7] .................................................. A61N 1/10
(52) U.S. Cl. ........................................................ 607/46
(58) Field of Search .............................. 607/1–3, 34, 36, 607/46, 115–118, 22, 50, 33; 129/898, 899; 128/898, 899

(56) References Cited

U.S. PATENT DOCUMENTS

| 3,157,181 A |   | 11/1964 | McCarty |   |
|---|---|---|---|---|
| 3,942,535 A | * | 3/1976 | Schulman | 607/33 |
| 4,306,561 A | * | 12/1981 | de Medinaceli | 606/22 |
| 4,919,140 A | * | 4/1990 | Borgens et al. | 607/50 |
| 6,051,017 A | * | 4/2000 | Loeb et al. | 607/1 |

OTHER PUBLICATIONS

A. A. Al–Majed, C. M. Neumann, E. Brustein, and T. Gordon. Brief Electrical Stimulation Promotes the Speed and Accuracy of Motor Axonal Regeneration. *The Journal of Neuroscience* 20 (7):2602–2608, 2000.

M. Bondoux–Jahan and A. Sebille. Conditioning lesion effects on rat sciatic nerve regeneration are influenced by electrical stimulation delivered to denervated muscles. *Brain Res* 490:350–354, 1989.

J. M. Byers, K. F. Clark, and G. C. Thompson. Effect of Pulsed Electromagnetic Stimulation on Facial Nerve Regeneration. *Otolaryngology, Head and Neck Surgery* 124 (4):383–389, 1998.

P. G. Cordeiro, B. R. Seckel, C. D. Miller, P. T. Gross, and R. E. Wise. Effect of a High–Intensity Static Magnetic Field on Sciatic Nerve Regeneration in the Rat. *Plastic and Reconstructive Surgery* 83 (2):301–308, 1989.

(Continued)

*Primary Examiner*—George Manuel
(74) *Attorney, Agent, or Firm*—McDermott Will & Emery

(57) ABSTRACT

Recovery from peripheral nerve and nerve plexus injuries is usually slow and incomplete because the regenerating motor axons often head erroneously toward sensory receptors rather than muscle fibers and because the target muscles atrophy while waiting for the slow process of reinnervation. Research has suggested that electrical stimulation with different waveforms and temporal patterns at different times during the regeneration process might improve the clinical outcome through various mechanisms, but a practical means to deliver such stimulation has been lacking. This invention teaches the use of miniature electrical stimulators that can be implanted alongside the injured nerve(s) at the time of surgical repair and that can be powered and controlled by transmission of radiofrequency energy from outside the body so as to provide a variety of electrical stimuli at different times during the recovery process.

30 Claims, 1 Drawing Sheet

OTHER PUBLICATIONS

S. Y. Fu and T. Gordon. Contributing Factors to Poor Functional Recovery after Delayed Nerve Repair: Prolonged Denervation. *The Journal of Neuroscience* 15 (5):3886–3895, 1995.

A. F. Hottinger, M. Azzouz, N. Deglon, P. Aebischer, and A. D. Zurn. Complete and Long-Term Rescue of Lesioned Adult Motoneurons by Lentiviral Mediated Expression of Glial Cell Line–Derived Neurotrophic Factor in the Facial Nucleus. *The Journal of Neuroscience* 20 (15):5587–5593, 2000.

H. Ito and C. A. Bassett. Effect of Weak, Pulsing Electromagnetic Fields on Neural Regeneration in the Rat. *Clin Orthop Rel Res* 181:283–290, 1983.

S. Manivannan and S. Terakawa. Rapid Sprouting of Filopodia in Nerve Terminals of Chromaffin Cells, PC12 Cells, and Dorsal root Neurons Induced by Electrical Stimulation. *The Journal of Neuroscience* 14 (10):5917–5928, 1994.

W. A. Nix and H. C. Hope. Electrical Stimulation of Regenerating Nerve and its Effect on Motor Recovery. *Brain Res* 272 (1):21–25. 1983.

M. G. Orgel, W. J. O'Brien, and H. M. Murray. Pulsing Electromagnetic Field Therapy in Nerve Regeneration: An Experimental Study in the Cat. *Plastic and Reconstructive Surgery* 73 (2):173–183, 1984.

B. F. Sisken, J. Walker, and M. Orgel. Prospects on Clinical Applications of Electrical Stimulation for Nerve Regeneration. *Journal of Cellular Biochemistry* 52:404–409, 1993.

H. B. Williams. A Clinical Pilot Study to Assess Functional Return Following Continuous Muscle Stimulation After Nerve Injury and Repair in the Upper Extremity Using a Completely Implantable Electrical System. *Microsurgery* 17:597–605, 1996.

H. B. Williams. The Value of Continuous Electrical Muscle Stimulation Using a Completely Implantable System in the Preservation of Muscle Function Following Motor Nerve Injury and Repair: An Experimental Study. *Microsurgery* 17:589–596, 1996.

\* cited by examiner

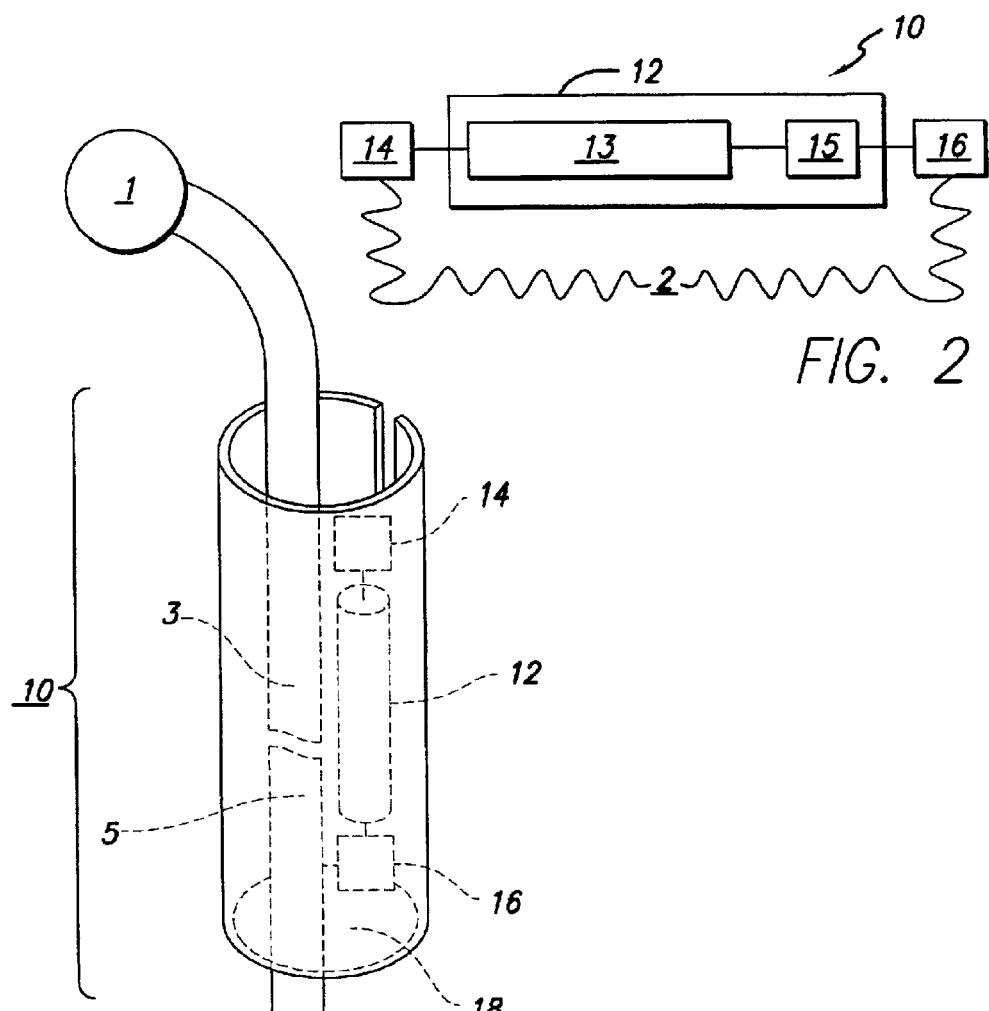
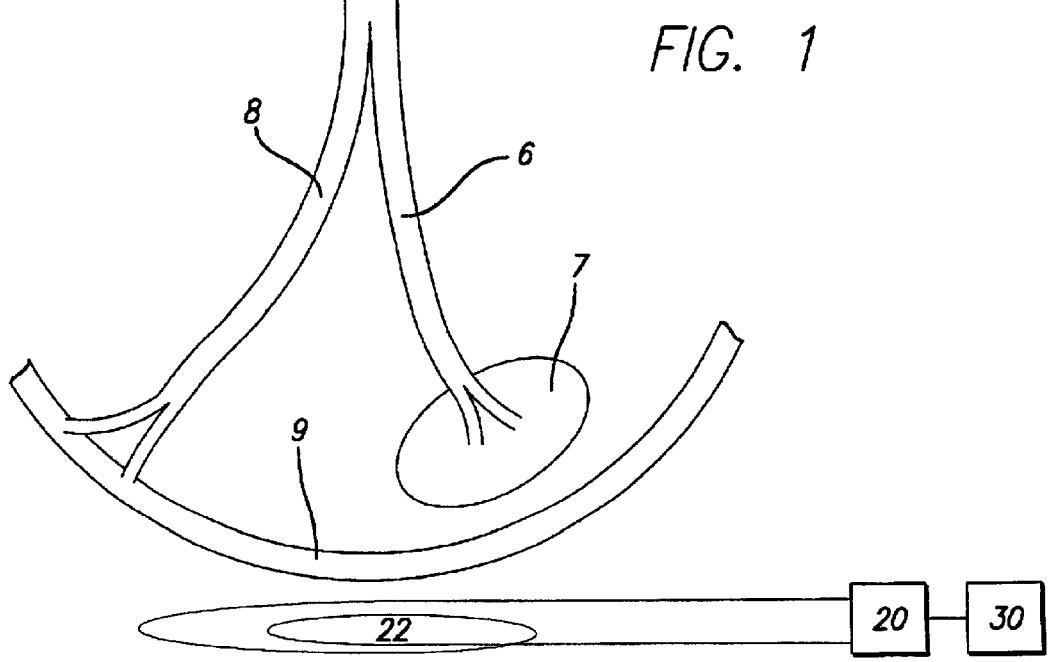
FIG. 2
FIG. 1

SYSTEM AND METHOD FOR PROVIDING RECOVERY FROM MUSCLE DENERVATION

RELATED APPLICATIONS

This application claims the filing date benefit of U.S. Provisional Application No. 60/255,284, filed on Dec. 13, 2000, entitled "Electrical Stimulator That Enhances Recovery from Muscle Denervation," the contents of which are incorporated herein.

BACKGROUND OF THE INVENTION

1. Field of the Invention

The present invention relates to a biomedical device designed for providing stimulation to initiate neuromuscular recovery following peripheral nerve injury or surgical repair.

Especially, the present invention relates to an electrical stimulator system, that is implantable within a body, for applying electrical stimulation to initiate neuromuscular recovery at an affected area in the body.

2. General Background

The central nervous system is connected to the muscles, skin and other organs of the body by peripheral nerves from the spinal cord and brainstem to various peripheral structures and organs. Most such nerves arise from a nerve plexus, where sensory and motor axons bound for various destinations become highly intermingled.

The sensory axons arise from primary sensory cell bodies located in or near the central nervous system. They extend outward to innervate various sensory receptor structures in skin and muscles, where they are excited to produce electrical impulses that are conducted back along the sensory axon and into the central nervous system. The motor axons arise from the cell bodies of motoneurons that are located in the central nervous system and that extend into muscles where they make synaptic connections with muscle fibers.

When the central nervous system makes a muscle contract, it does so by sending electrical impulses to those neuromuscular synapses at the ends of the motor axons of the motoneurons. This results in the release of a chemical transmitter, which in turn induces an electrical signal in the muscle fibers. This electrical signal acts through other chemical pathways within the muscle fiber to result in generation of contractile force.

When a peripheral nerve or nerve plexus is cut, crushed, or damaged, electrical impulses cease to pass through both the sensory and motor axons at the site of injury. In the part of the peripheral nerve that is distal to the injury, both the sensory and motor axons may be cut off from their cell bodies, which normally provide essential chemicals required to maintain the axons. Thus, these axons degenerate and die within a few days of injury, a process referred to as "Wallerian degeneration." In the proximal stump of the injured peripheral nerve, the damaged axons typically seal themselves off and undergo a complex sequence of changes in preparation for regrowth back toward the sensory and motor structures that they originally innervated.

Throughout the peripheral nerves, the larger axons (responsible for motor functions and important sensory functions) are surrounded by sheaths composed of specialized supporting cells called Schwann cells. When the distal portion of an injured axon dies, these Schwann cell sheaths remain intact indefinitely.

Schwann cell sheaths surrounding sensory and motor axons appear to have different properties. They undergo various chemical changes that may play an important role in facilitating the regeneration of the damaged sensory and motor axons by supplying guidance mechanisms and trophic factors. The regrowing axons must locate and then grow into and through the correct type of Schwann cell sheaths, which direct them toward denervated skin, muscles and any other organs to which the peripheral nerve should be connected.

Unfortunately, many of the motor axons that normally convey electrical commands to muscle fibers start to grow into the open ends of Schwann cell sheaths that once surrounded sensory axons. These sensory sheaths direct the regenerating motor axons toward the many sensory receptors in muscle and skin. Conversely, many of the regenerating sensory axons enter sheaths that direct them toward muscle fibers, with which they cannot make effective synapses. These inappropriate connections are not useful in reestablishing function.

In addition, regrowth of peripheral nerve axons occurs slowly from the site of injury (roughly 2–3 millimeters a day). During the time required for regenerating motor axons to reach denervated muscle fibers, the denervated muscle fibers are not receiving any chemical or electrical activation. Muscle fibers that are not activated occasionally will atrophy, becoming small and weak and sometimes disappearing entirely, to be replaced by fat and connective tissue. If the peripheral nerve injury is far from the denervated muscles or if the regenerative process is delayed, the muscle fibers may be so atrophic by the time they are reinnervated that recovery of motor function will be slow and incomplete.

Many of the processes that govern both the normal function of muscles and nerves and their recovery from a denervation injury are believed to be influenced by electrical activity of the nerves. Recently, it has been reported that electrical stimulation of the proximal stump of a cut nerve shortly after it has been surgically repaired reduces the number of motor axons that wind up regenerating into cutaneous sensory nerve branches. The Schwann cell sheaths surrounding sensory versus motor axons appear to react differently during the processes of denervation and reinnervation, with motor sheaths increasing the production of biochemical substances, such as the carbohydrate epitope named L2/HNK-1. Cell bodies of motoneurons are also affected by the backward or antidromic excitation of cell bodies by electrical stimulation. Stimulated cells increase their genetic expression of signaling and trophic molecules such as BDNF and its receptor trkB.

Electrical stimulation appears to augment difference in the way that motor and sensory axons recover, which contributes to the accuracy of sensory and motor reinnervation. Other studies have claimed that the application of weak negative electrical fields along the axis of nerve regeneration or pulsed electromagnetic fields accelerates the rate of outgrowth of the regenerating axons. Electrical activation of the regenerating axons may also accelerate their rate of maturation, i.e. enlargement of axon caliber, remyelination and increase in conduction velocity. Still other studies indicate that the process of recovery from muscle atrophy can be augmented by using electrical stimulation to exercise atrophic muscle fibers once their efferent neural connections have been reestablished.

However, it is difficult to stimulate peripheral nerves, particularly main nerves and nerve plexuses located deep within the proximal limbs or trunk. Although some methods have been suggested, each has at least some of the following important disadvantages:

(i) Electrical stimulation can be applied to the surface of the skin, but the intensity must be very high to influence the target nerves. This intensity is likely to produce uncomfortable sensations from stimulation of intact skin nerves and even irritation or damage of the underlying skin. It is also difficult to determine the effective level of stimulation intensity, which must be adjusted each time the electrodes are reapplied.

(ii) Electrical stimulation can be applied at the time of surgery when the nerve is exposed but it is generally important to minimize the duration of surgical procedures to minimize post-operative complications and morbidity. This is particularly true when the surgical repair is performed with tourniquet occlusion of the blood supply to the limb or when the patient requires complex medical and surgical care to deal with multiple consequences of a traumatic injury.

(iii) A conventional electrical stimulator can be implanted into the body and an electrode can be implanted on or near the repaired nerve and connected to the stimulator by an electrical lead. However, this considerably complicates the scope of the repair surgery and risks further damage or infection of the repaired nerve and surrounding tissues, which may already be highly traumatized by the original injury.

(iv) It is possible to implant electrodes temporarily at the site of the surgical repair, bringing electrical leads out through the skin of the surgical incision or another percutaneous site for connection to a conventional electrical stimulator. However, this poses the dangers of inadvertent mechanical traction or spread of infection to the already traumatized tissues surrounding the injured and repaired nerve. It also complicates general nursing and wound care during the extended period during which treatment may be desired.

Further, A. A. Al-Majed, C. M. Neumann, E. Brustein, and T. Gordon. Brief Electrical Stimulation Promotes the Speed and Accuracy of Motor Axonal Regeneration. *The Journal of Neuroscience* 20 (7):2602–2608, 2000 have demonstrated that stimulation produces augmentation of motor axonal regeneration into muscle nerves when delivered at the time of the nerve repair. No system however was described for effecting this in practice.

SUMMARY OF THE INVENTION

Clearly there is a need for a safe implantable system that may provide electrical stimulation at various times after injury to initiate and/or augment neuromuscular recovery at an affected area in the body Accordingly, it is an aspect of the invention to use electrical stimulation to enhance motor recovery following peripheral nerve injury or surgical repair.

In one embodiment, the invention provides a device and method for applying electrical stimulation conveniently and throughout the recovery period. The device is an electrical stimulator system comprising an electronic assembly generating electrical currents having variable parameters such as intensity, period, duration, shape, and temporal pattern, a first electrode that whereby said electrical currents are applied to the tissues of the body, and a second electrode providing a return path for the electrical currents, wherein the first electrode, the second electrode, and the electronic assembly are implanted within the body.

In another embodiment, the invention provides a device and method for applying electrical stimulation conveniently and throughout the recovery period. The device is an electrical stimulator system comprising a first electrode generating a signal having variable parameters such as intensity, period, duration, shape, and temporal pattern, a second electrode providing a return path for the signal, an electronic assembly for storing energy in a capacitance associated with the first electrode and for releasing energy into the body, all being implanted within a body.

Additionally, the invention allows adjustment of waveforms and patterns of electrical stimulation to different phases of nerve regeneration and muscle reinnervation and recovery from atrophy.

The invention also includes a method for determining the state of recovery of the innervation and contractile capabilities of the muscle. This method comprises applying at least one stimulus pulse through the system at a level of intensity sufficient to evoke an action potential in the nerve. The response to this stimulus pulse can then be measured by conventional means, including but not limited to electromyography to assess the synaptic connection of motor axons to muscle fibers and muscle force recording to assess the mechanical strength and fatigability of the reinnervated muscle fibers.

BRIEF DESCRIPTION OF THE DRAWINGS

In order that the manner in which the above-recited advantages and objects of the invention are attained, as well as others which will become apparent, more particular description of the invention briefly summarized above may be had by reference to the specific embodiments thereof that are illustrated in the appended drawings. It is to be understood, however, that the appended drawings illustrate only typical embodiments of the invention and are therefore not to be considered limiting of its scope, for the invention may admit to other, equally effective embodiments.

In the drawings:

FIG. 1 depicts one embodiment of the electrical stimulator system comprising first and second electrodes, an electronic assembly, a flexible sheath, an inductive coupling, a controller and a programmer.

FIG. 2 is a representation of the fully implanted electrical stimulator device.

DETAILED DESCRIPTION OF PREFERRED EMBODIMENTS OF THE INVENTION

The present invention provides a device capable of delivering therapeutic levels of electrical stimulation to a damaged nerve site. The device can be implanted within the body at the site of surgical repair for a damaged nerve. This minimizes any additional surgery that would be required to implant the stimulation circuitry and associated leads and electrodes, such as with other types of devices. A fully implantable stimulation device also minimizes potential damage to the nerve from infection or traction that may occur with percutaneous wire leads. Additionally, an implantable device of the present invention is also advantageous in that it can be used to provide controlled, accurate and reproducible stimulation throughout the period of nerve regeneration and functional recovery.

In one embodiment, an implantable electrical stimulator suitable for use in the present invention can be of the BION™ microstimulator type, also developed by the inventor of the present application. Description of BION microstimulator form factor and methods of its fabrication are described, for example, in U.S. Pat. No. 5,312,439, May 17, 1994, issued to Loeb et al. and U.S. Pat. Nos. 5,193,539 and 5,193,539, Mar. 18, 1993, issued to Schulman et al. The present invention includes use of this microstimulator for therapeutic delivery of electrical stimulation to a damaged peripheral nerve. The technique of wrapping the stimulating electrodes and target nerve in an electrically insulating sheath was patented by Loeb, U.S. Pat. No. 4,590,946, May 27, 1986.

Referring to FIG. 1, in one embodiment, the electrical stimulator 100 is in the form of a self-contained cylindrical module that has a size and shape suitable for implantation at the site of the surgical repair of the injured nerve. The proximal stump 3 of the nerve is connected to the central nervous system 1; the distal stump 5 of the nerve is connected to various muscles 7 and regions of the skin 9 by muscle nerves 6 and cutaneous nerves 8, respectively. An object of the treatment is to maximize the number of motor axons that regenerate correctly from proximal stump 3 across the site of the surgical repair and into the Schwann cell sheaths that used to contain motor axons innervating muscle fibers in the muscles 7. The treatment begins with implanting electrical stimulator(s) 10 so that it (they) straddle(s) the surgical repair connecting the proximal stump 3 to the distal stump 5 of the injured nerve.

As shown in FIG. 2, the electrical stimulator 10 consists of electronic assembly, or electronic circuit 12 connected to proximal electrode 14 and distal electrode 16. There is an electrical signal generator 13 and a blocking capacitor 15 to prevent net direct current flow through the electrodes 14 and 16, and the surrounding conductive tissues of the body 2. The capacitor 15 is discharged intermittently for resetting purposes. This system provides a non-pulsatile field for a sufficient length of time. Electrical stimulator 10 is capable of producing a signal, with variable parameters such as intensity, shape, duration, period and temporal patterns, in and around the injured nerve. Advantageously, the signal is an electrical current that passes through the electrodes 14 and 16 and the intervening tissues of the body, including the nerve that has been injured. If desired, the electrical currents can be confined more closely to the site of the repaired nerve by the application of sheath 18. In a preferred embodiment, sheath 18 consists of a loose wrapping of a flexible, dielectric membrane such as, for example, a silicone elastomer sheet.

In another embodiment, proximal electrode 14 is a tantalum capacitor electrode, which is anodized so that it can be charged to a substantial positive voltage (typically +17VDC) without producing electrolytic reactions with the saline body fluids. As described in greater detail below, this permits a range of different output waveforms of electrical current to be produced without risk of generating net direct current in one direction, which is known to be potentially damaging to both electrodes and living tissues. Distal electrode 16 can be made from iridium, which maintains neutral polarization regardless of the level of charging of the tantalum capacitor electrode, as described in U.S. Pat. No. 5,312,439 (Loeb) and incorporated herein by reference. Electronic assembly 12 stores energy in the capacitance of proximal electrode 14 by steadily applying a specified anodal current until it is charged to the compliance voltage produced from the applied RF field generated by coil 22. Pulsatile stimulation is generated by discharging the positively charged proximal electrode 14 through the intervening body fluids to distal electrode 16.

Electrical stimulator 10 receives power and command signals generated outside the body by controller 20 through inductive coupling of a radio-frequency electrical field generated in coil 22. Controller 20 can be programmed with one or more patterns of electrical stimulation to be delivered to the injured nerve. Such programming can be performed by a physician or other medical practitioner by use of, for example, an electronic programmer 30. When the electrical stimulation treatment is being delivered, controller 20 can be operated by a caregiver or the patient himself or herself.

In another preferred embodiment, the electrical stimulation would be applied according to the following schedule:

Within the first week after the surgical repair of the nerve, trains of short duration pulses are delivered at an intensity sufficient to evoke action potentials in the large diameter motor axons in proximal stump 3. Typical values would be 1 hour of continuous stimulation at 20 pps with each pulse consisting of 4 mA cathodal current applied through proximal electrode 14 and returned through distal electrode 16.

The present invention shows that the system, and method for stimulation is effective if delivered after nerve repair. This may be at significant time periods after the nerve repair, namely about 1 to about 24 hours after the nerve repair. This time period delay is often a more feasible methodology and system in clinical practice. Prior to the present invention this had never before been thought feasible.

If the surgical repair occurred soon enough after the nerve injury that there are still axons capable of conducting action potentials in distal stump 5, then the stimulation intensity should be increased sufficiently that the anodal current returning through distal electrode 16 elicits action potentials in the distal motor axons, as determined by contractions produced in muscles 7. Anodal current will stimulate axons by creating "virtual cathodes" along the axons somewhat distal from the point of application of the anodal current at distal electrode 16.

After the distal motor axons cease responding to pulsatile electrical stimulation, electrical stimulator 10 is used to create long duration, low amplitude potential gradients in which distal electrode 16 functions as a cathode. This can be accomplished by applying a brief, high intensity pulse to discharge the capacitance of proximal electrode 14 and then applying a low level of anodal recharge current such as 10 $\mu$A until the capacitance is fully recharged. This creates potential gradients in the peripheral nerve sufficient to enhance the outgrowth of neuritis.

The time at which motor axons first reinnervate muscles 7 is identified by noting the onset of evoked contractions in those muscles. At that time, the stimulation program is changed to provide a pattern of muscle activation that will tend to build up the cross-sectional area and contractile strength of the atrophied muscles. One such pattern would be 5 second trains of pulses at 5 pps every 10 s for 30 minutes three times a day.

After muscles 7 begin to be reinnervated, electrical stimulator 10 is used in conjunction with conventional clinical instrumentation to record and quantify the electromyogram and contractile force produced by the muscles 7 so as to document the rate and amount of recovery of muscle function. Such information is useful for the design and evaluation of further electrical, surgical and physical therapy that may be indicated.

It is an advantage of our invention that the schedule for applying electrical therapy and the parameters of that therapy can be altered freely by the therapist to take advantage of additional information that the therapist may have regarding the patient's history or condition and new advances in scientific and medical knowledge regarding optimal treatment of the patient's condition. The schedule and parameters of treatment described above are consistent with some current reports of promising treatments, but it will be obvious to anyone skilled in the art that our invention can be used in a variety of ways to achieve the stated object of enhancing the process of motor recovery following peripheral nerve injury and surgical repair.

While the specification describes particular embodiments of the present invention, those of ordinary skill can devise variations of the present invention without departing from the inventive concept. For example, a plurality of such implantable electrical stimulators may be positioned at different locations, and the signals associated with each of these stimulators may be controlled by a separate or central controller. The effective stimulus for the generation of action potentials and other trophic effects in axons is likely to be related to the strength, gradient and temporal properties of the electrical field created in the vicinity of the axons, which can be shaped by the constructive and destructive summation of electrical currents introduced by a plurality of synchronously activated electrical stimulators. In addition, the treatments described in this disclosure could be provided by conventional laboratory instrumentation and medical stimulators designed for other clinical applications such as transcutaneous electrical nerve stimulation (TENS) commonly used to reduce chronic pain.

We claim:

1. An electrical stimulator system for augmenting recovery from muscle denervation, the electrical stimulator system comprising: a first electrode adjacent a proximal stump of a nerve and for emitting a signal having at least one variable parameter; a second electrode providing a return path for the signal; an electronic assembly for generating the signal; the first electrode, the second electrode, and the electronic assembly adapted to be positioned within the body; and said signal propagating through electrically conductive tissues of the body and evoking an action potential in at least one motor axon, the motor axon regenerating from the proximal stump, so as to augment recovery from muscle denervation.

2. The electrical stimulator system according to claim 1, wherein one of the electrodes stores energy by capacitive means.

3. The electrical stimulator system according to claim 2, wherein the first electrode is a tantalum capacitor electrode.

4. The electrical stimulator system according to claim 1 further comprising: an electronic programmer for programming variable parameters; a controller having an input connected to the output of the electronic programmer, and supplying a command signal at its output to an inductive coupling; and said at least one of the variable parameters being included in the command signal.

5. The electrical stimulator system according to claim 4, wherein the inductive coupling applies a radio frequency field to the electronic assembly.

6. The electrical stimulator system according to claim 1, wherein the signal is a current.

7. The electrical stimulator system according to claim 6, further comprising a flexible dielectric membrane as a sheath to confine the current more closely with the nerve.

8. The electrical stimulator system according to claim 1, wherein the second electrode is made of iridium.

9. The electrical stimulator system according to claim 1, wherein the second electrode maintains a neutral polarization relative to the first electrode.

10. The electrical stimulator system according to claim 1, wherein said at least one variable parameter being at least one of intensity, duration, shape, and temporal pattern.

11. The electrical stimulator system according to claim 1, including a capacitor in series with the electrodes for the purpose of preventing net direct current flow through the electrodes and tissues.

12. The method or treatment of injuries to peripheral nerves to provide recovery from muscle denervation employing the stimulator system according to claim 1, further comprising the step of recording and quantifying an electromyogram and contractile forces produced by the muscle in response to the action potentials.

13. The method or treatment of injuries to peripheral nerves to augment recovery from muscle denervation employing the stimulator system according to claim 1, further comprising the step of applying current so as to create potential gradients in the peripheral nerve sufficient to enhance the outgrowth of neurites.

14. An electrical stimulator system for augmenting recovery from muscle denervation, the electrical stimulator system comprising: a first electrode adjacent a proximal stump of a nerve and generating a signal having at least one variable parameter; a second electrode for receiving the signal; an electronic assembly for storing energy in a capacitance, said energy being a source for the signal; the first electrode, the second electrode, and the electronic assembly adapted to be positioned within the body; said signal propagating through electrically conductive tissues in the body and evoking an action potential in at least one motor axon, the motor axon regenerating from the proximal stump, so as to augment recovery from muscle denervation.

15. The electrical stimulator system according to claim 14 further comprising: an electronic programmer for programming variable parameters; a controller having an input connected to an output of the electronic programmer, and supplying a command signal at its output to an inductive coupling; and said at least one of the variable parameters being included in the command signal.

16. The electrical stimulator system according to claim 15, wherein the inductive coupling applies a radio frequency field to the electronic assembly.

17. The electrical stimulator system according to claim 14, wherein the signal is a current.

18. The electrical stimulator system according to claim 17, further comprising a flexible dielectric membrane as a sheath to confine the current more closely with the nerve.

19. The electrical stimulator system according to claim 14, wherein the second electrode is made of iridium.

20. The electrical stimulator system according to claim 14, wherein the second electrode maintains a neutral polarization relative to the first electrode.

21. The electrical stimulator system according to claim 14, wherein the electronic sensor is positioned within the body.

22. The electrical stimulator system according to claim 14, wherein said at least one variable parameter being at least one of intensity, period, duration, shape, and temporal pattern.

23. A system for treatment of a surgically repaired peripheral nerve to augment recovery from muscle denervation, the system comprising:
   an electronic device adapted to be implanted in the body in the vicinity of the joined stumps peripheral nerve, said electronic device producing electrical currents in the body that flow in part through the peripheral nerve; and
   an electronic controller located outside the body for controlling the strength, duration and temporal patterning of said electrical currents.

24. A method for treatment of injuries to a peripheral nerves in the vicinity of joined stumps to augment recovery from muscle denervation, the method comprising the step of:

applying a train of stimulating pulses through a first electrode positioned in the vicinity of the joined stumps at a predetermined intensity to evoke action potentials in at least one motor axon in one of the joined stump; the pulses being applied at a time period after effecting nerve repair.

25. A method as claimed in claim 24 including supplying a brief and high intensity stimulating pulse by discharging a capacitance in the first electrode.

26. A method as claimed in claim 24 wherein the time period is between about 1 hour and 24 hours.

27. The method or treatment of injuries to peripheral nerves to provide recovery from muscle denervation according to claim 24, further comprising the step of recording and quantifying an electromyogram and contractile forces produced by the muscle.

28. The method or treatment of injuries to peripheral nerves to provide recovery from muscle denervation according to claim 24, further comprising the step of increasing the stimulation pulse intensity to elicit action potentials in distal motor axons.

29. A method for determining the state of recovery from a peripheral nerve injury, the method comprising the steps of: applying a train of stimulating pulses from an implanted device at a predetermined intensity to evoke action potentials in at least one motor axon in a proximal stump; and effecting at least one of recording or quantifying at least one of an electromyogram or contractile forces produced by the muscle.

30. A method for treatment of injuries to peripheral nerves to augment recovery from muscle denervation, the method comprising:

applying a non-pulsatile electrical field for a sufficient length of time after effecting nerve repair by means of a fully implanted device, wherein a capacitor prevents net direct current flow through electrodes and/or conductive tissue of the body, and said capacitor is discharged intermittently for resetting purposes.

* * * * *